United States Patent
Narimatsu et al.

[11] Patent Number: 5,439,002
[45] Date of Patent: Aug. 8, 1995

[54] BLOOD PRESSURE MONITOR SYSTEM

[75] Inventors: Kiyoyuki Narimatsu, Kasugai; Hideo Nishibayashi, Inuyama, both of Japan

[73] Assignee: Colin Corporation, Komaki, Japan

[21] Appl. No.: 330,661

[22] Filed: Oct. 28, 1994

[30] Foreign Application Priority Data

Nov. 8, 1993 [JP] Japan .................. 5-278661

[51] Int. Cl.[6] ............................................. A61B 5/00
[52] U.S. Cl. ...................... 128/672; 128/687; 128/690
[58] Field of Search .................. 128/672, 680–690, 128/748

[56] References Cited

U.S. PATENT DOCUMENTS

| | | | |
|---|---|---|---|
| 4,799,491 | 1/1989 | Eckerle | 128/672 |
| 4,836,213 | 6/1989 | Wenzel et al. | 128/687 |
| 5,101,829 | 4/1992 | Fujikawa et al. | |
| 5,119,822 | 6/1992 | Niwa. | |
| 5,179,956 | 1/1993 | Harada et al. | |

*Primary Examiner*—Lee S. Cohen
*Assistant Examiner*—Robert L. Nassa, Jr.
*Attorney, Agent, or Firm*—Oliff & Berridge

[57] ABSTRACT

A blood pressure monitor system including a pressure sensor having a press surface and including pressure sensing elements provided in the press surface; a pressing device which presses the pressure sensor against an artery via a body surface so that each pressure sensing element measures a pressure value at the body surface; a first device for determining an optimum pressing force of the pressing device at which a portion of a wall of the artery is flattened under the pressure sensor; a second device for changing pressing forces of the pressing device, and determining a point of inflection of a curve representing a relationship between the changed pressing forces and pressure values measured by the pressure sensor at the body surface; a third device for determining a correction value based on the pressure value of the determined point of inflection; and a blood-pressure determining device for operating the pressing device to maintain the determined optimum pressing force and press the pressure sensor against the artery via the body surface, and continuously determining intra-arterial blood pressure values of the artery by subtracting the correction value from the pressure values measured by the pressure sensor at the body surface.

13 Claims, 4 Drawing Sheets

BLOOD PRESSURE MONITOR SYSTEM

BACKGROUND OF THE INVENTION

1. Field of the Invention

The present invention relates to a blood pressure monitor system which continuously measures intra-arterial blood pressure of a living subject and particularly relates to the art of improving the accuracy of blood pressure measurement.

2. Related Art Statement

There has been proposed a blood pressure monitor system including a pressure sensor having a press surface and including one or more pressure sensing elements provided in the press surface; a pressing device which presses the pressure sensor against an arterial vessel of a living subject such as a patient via a body surface of the subject so that each pressure sensing element of the pressure sensor measures pressures at the body surface of the subject; pressing-force determining means for determining an optimum pressing force of the pressing device at which a portion of a wall of the artery is flattened under the pressure sensor pressed by the pressing device; and blood-pressure determining means for operating the pressing device to maintain the determined optimum pressing force and press the pressure sensor against the artery via the body surface or skin, and continuously determining intra-arterial blood pressure values of the artery, based on the pressure magnitudes or values measured by the pressure sensor at the body surface. An example of this monitor system is disclosed in U.S. Pat. No. 5,119,822 or U.S. Pat. No. 5,179,956.

In the above-indicated prior monitor system, the pressure sensor is pressed against the artery via the body surface or skin, such that the wall of the artery is partly flattened under the pressure sensor. Since the pressure values measured by the pressure sensor through the flattened wall of the artery are free from adverse influences of the tensile forces produced in the arterial wall, they well reflect intra-arterial blood pressure values of the artery. According to this blood pressure measurement principle, the prior monitor system continuously measures the blood pressure of the subject by using the pressure sensor pressed at the optimum pressing force.

Meanwhile, the experiments the present inventors conducted have elucidated that the blood pressure values continuously measured by the above-indicated prior monitor system tend to be higher than the blood pressure values measured using an inflatable cuff, and do not enjoy sufficiently high measurement accuracy. In this background, the present inventors have made various studies and experiments, and found that the soft and elastic subcutaneous tissue exists between the arterial vessel and the pressure sensor and that a "provisional" blood pressure measured by the pressure sensor, i.e., pressure sensing element positioned directly above the artery and pressed at the optimum pressing force contains both a "true" intra-arterial blood pressure of the artery and an "additional" pressure added thereto because of the elastic force of the subcutaneous tissue under the pressure sensor.

SUMMARY OF THE INVENTION

It is therefore an object of the present invention to provide a blood pressure monitor system which continuously measures intra-arterial blood pressure of a living subject with high accuracy.

The above object has been achieved by the present invention, which provides a blood pressure monitor system comprising: (a) a pressure sensor having a press surface and including at least one pressure sensing element provided in the press surface; (b) a pressing device which presses the pressure sensor against an arterial vessel of a living subject via a body surface of the subject so that the pressure sensing element of the pressure sensor measures a pressure value at the body surface of the subject; (c) pressing-force determining means for determining an optimum pressing force of the pressing device at which a portion of a wall of the arterial vessel of the subject is flattened under the pressure sensor pressed by the pressing device; (d) inflection-point determining means for changing pressing forces of the pressing device applied to the pressure sensor, and determining a point of inflection of a curve representing a relationship between the changed pressing forces of the pressing device and pressure values measured by the pressure sensor at the body surface of the subject; (e) correction-value determining means for determining a correction value based on the pressure value of the determined point of inflection; and (f) blood-pressure determining means for operating the pressing device to maintain the determined optimum pressing force and press the pressure sensor against the arterial vessel of the subject via the body surface of the subject, and continuously determining intra-arterial blood pressure values of the arterial vessel of the subject by subtracting the correction value from the pressure values measured by the pressure sensor at the body surface of the subject.

In the blood pressure monitor system constructed as described above, the correction-value determining means determines a correction value based on the pressure value of the determined inflection point, and the blood-pressure determining means operates the pressing device to maintain the determined optimum pressing force and press the pressure sensor against the artery via the body surface or skin, and continuously determines intra-arterial blood pressure values of the artery by subtracting the correction value from the pressure values measured by the pressure sensor at the body surface. The correction value corresponds to the above-explained "additional" pressure added to the "true" intra-arterial blood pressure of the artery because of the elasticity of the subcutaneous tissue occurring between the artery and the pressure sensor. Since the additional pressure is removed by subtracting the correction value from the provisional blood pressure values measured by the pressure sensor, the present monitor system enjoys the sufficiently high accuracy of blood pressure measurement.

In a preferred embodiment of the present invention, the correction-value determining means comprises: a memory which stores a plurality of pressure correcting curves each of which represents a relationship between correction values and pressing forces of the pressing device; selecting means for selecting one of the pressure correcting curves which provides a same difference between a first correction value corresponding to the pressing force of the determined point of inflection and a second correction value corresponding to the determined optimum pressing force of the pressing device, as an actual difference between the pressure value of the point of inflection and the pressure value corresponding to the optimum pressing force of the pressing device;

and determining means for determining, as the correction value, the second correction value corresponding to the optimum pressing force of the pressing device, according to the selected one pressure correcting curve. Each of the pressure correcting curves represents a relationship between the pressing forces of the pressing device and the above-explained "additional" pressure values that increase because of the elasticity of the subcutaneous tissue as the pressing forces of the pressing device increase.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
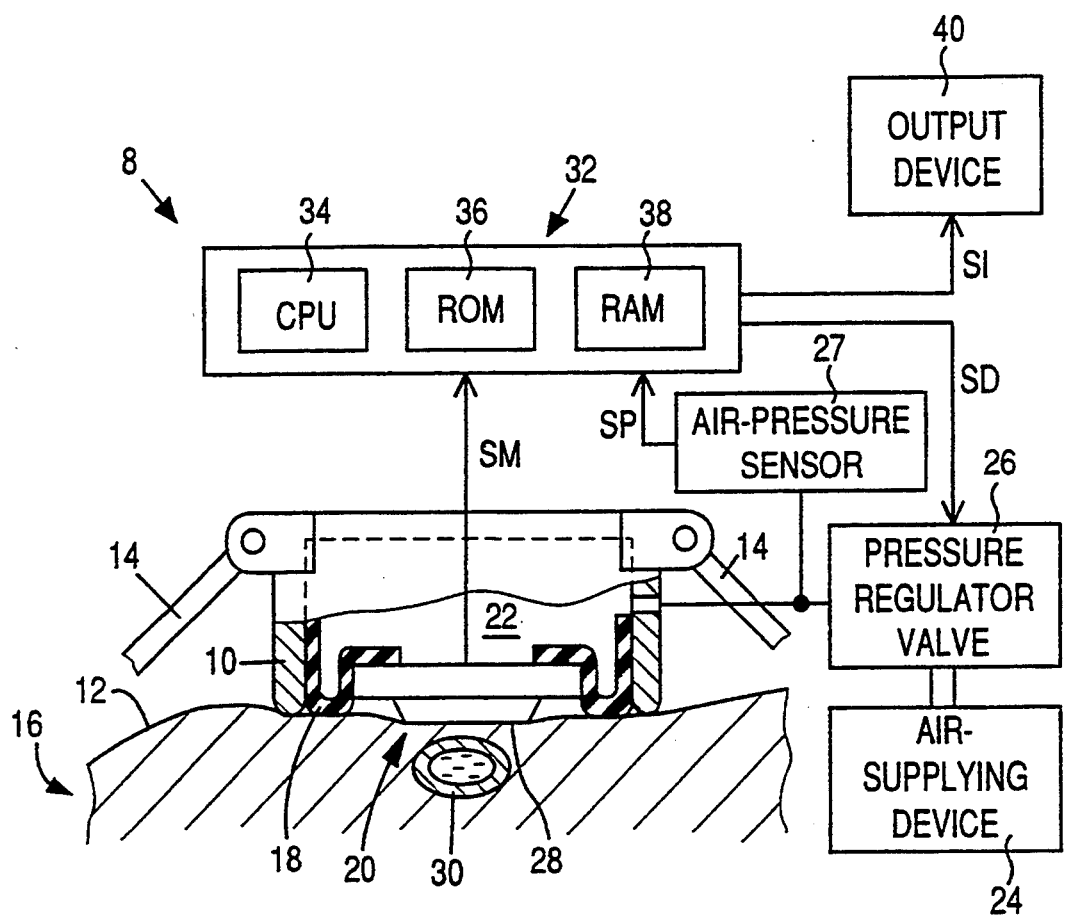
FIG. 1 is a diagrammatic view of a blood pressure monitor system embodying the present invention.
Figure 2:
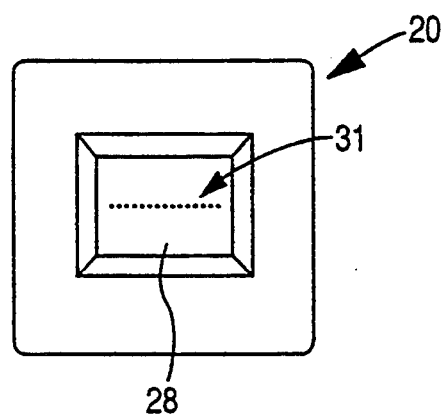
FIG. 2 is a bottom view of a pulse wave sensor of the monitor system of FIG. 1.

Referring to FIGS. 1 and 2, there is shown a blood pressure monitor system 8 embodying the present invention. In FIG. 1, reference numeral 10 designates a container-like housing which is open at one end thereof. The housing 10 is detachably set on a wrist 16 of a living subject such as a patient, with a pair of bands 14, 14, such that the open end of the housing 10 is held in contact with a body surface or skin 12 of the subject. A pulse wave sensor 20 is secured to a flexible diaphragm 18 which is supported by inner surfaces of side walls of the housing 10 and which closes the open end of the housing 10, such that the pulse wave sensor 20 is displaceable relative to the housing 10 and is advanceable out of the open end of the housing 10. The housing 10, diaphragm 18, and pulse wave sensor 20 cooperate with each other to define a pressure chamber 22 which is supplied with a pressurized fluid such as a pressurized air from an air-supplying device 24 via a pressure regulator valve 26. Thus, the pulse wave sensor 20 is pressed against the skin 12 with a pressing force corresponding to an air pressure in the pressure chamber 22 (hereinafter, referred to as the "chamber pressure HDP"). In the present embodiment, the housing 10, diaphragm 18, air-supplying device 24, pressure regulator valve 26, and others cooperate with each other to provide a pressing device for pressing the pulse wave sensor 20 against the skin 12. An air-pressure sensor 27 is provided to measure the chamber pressure HDP. The air-pressure sensor 27 supplies a pressure signal, SP, representing the measured chamber pressure HDP, to a control device 32.

The pulse wave sensor 20 shown in FIG. 2 includes a chip of a semiconductor material such as a monocrystalline silicon. A predetermined number of pressure sensing (PS) elements (e.g., thirty elements) 31 such as pressure sensing diodes are provided in an array in a press surface 28 of the semiconductor chip. With the pulse wave sensor 20 being pressed against the skin 12 in the above-described manner, the array of PS elements 31 substantially perpendicularly intersects a radial artery 30 of the wrist 16, so that each of the PS elements 31 detects an oscillatory pressure wave, i.e., pressure pulse wave that is produced from the radial artery 30 in synchronism with heartbeats of the subject and is transmitted to the skin or body surface 12. The individual PS elements 31 are spaced by sufficiently small distances from each other in the array thereof, so that a sufficiently large number of PS elements 31 are positioned directly above the artery 30. The overall length of the array of PS elements 31 is greater than the diameter or lumen of the artery 30.

The semiconductor chip of the pulse wave sensor 20 has a thickness of about 300 microns ($\mu$m). An elongate recess (not shown) is formed in a back surface of the chip opposite to the press surface 28, so that the chip has an elongate thin portion having a thickness of about several to ten and several microns ($\mu$m). In this elongate thin portion, the thirty PS elements 31 are provided at regular intervals of distances, e.g., intervals of about 0.2 mm. Each PS element 31 is constituted by a resistance bridge including four strain-resisting elements produced by a well-known semiconductor manufacturing process such as diffusion or injection of impurities. The PS element or resistance bridge is disclosed in U.S. Pat. No. 5,101,829 assigned to the Assignee of the present application. Each PS element 31 generates an electric signal whose magnitudes correspond to pressure magnitudes input thereto from the radial artery 30 via the skin 12, i.e., generates a pulse wave signal, SM, representing the pressure pulse wave produced from the artery 30. The pulse wave signal SM is supplied to the control device 32.

The control device 32 includes a microcomputer comprised of a central processing unit (CPU) 34, a read only memory (ROM) 36, and a random access memory (RAM) 38. The CPU 34 processes input signals according to control programs pre-stored in the ROM 36 by utilizing a temporary-storage function of the RAM 38. Specifically described, the CPU 34 determines an optimum chamber pressure, $HDP_S$, as an optimum pressing force to be applied to the pulse wave sensor 20, and selects an optimum PS element 31a from the thirty PS elements 31, each based on the pulse wave signals SM supplied from the thirty PS elements 31 to the control device 32 while the chamber pressure HDP is continuously increased. The CPU 34 controls the pressure regulator valve 26 to hold the chamber pressure HDP at the thus determined optimum value $HDP_S$ and thereby obtain a pressure pulse wave of the subject as the pulse wave signal SM supplied from the thus selected optimum PS element 31a pressed with the optimum pressure $HDP_S$. The CPU 34 controls an output device 40 to display a waveform representing intra-arterial blood pressure values, $P_{BP}$, of the radial artery 30, and record the same on a record sheet (not shown), each based on the pulse wave signal SM supplied from the optimum PS element 31a. An upper peak and a lower peak of each of successive pulses of the waveform displayed and recorded by the output device 40 correspond to a systolic blood pressure, $P_{SYS}$, and a diastolic blood pressure, $P_{DIA}$, in the artery 30. The output device 40 displays, in digits, the systolic and diastolic blood pressure values $P_{SYS}$, $P_{DIA}$ for each one pulse, and additionally displays, using points or other symbols, respective time-wise changes of the systolic and diastolic blood pressure values $P_{SYS}$, $P_{DIA}$ for the successive pulses.

When the radial artery 30 under the skin 20 is pressed by the pulse wave sensor 20 with the optimum chamber pressure $HDP_S$, a portion of the wall of the artery 30 is flattened as shown in FIG. 1. Pressure magnitudes or values, P, measured by the pulse wave sensor 20 through the flattened wall of the artery 30 are free from adverse influences of the tensile forces produced in the wall of the artery 30, and accordingly they reflect the intra-arterial blood pressure values of the artery 30. According to this blood pressure measurement principle, the control device 32 controls the present monitor system 8 to continuously measure the blood pressure values $P_{BP}$ in the artery 30 of the subject.

The various functions of the present blood pressure monitor system 8 for carrying out the continuous blood pressure measurement of a living subject are summarized as follows: The pulse wave sensor 20 functioning as a pressure sensor is pressed, at the optimum chamber pressure $HDP_S$, i.e., optimum pressing force of the pressing device 10, 18, 24, 26 determined by the control device 32 functioning as pressing-force determining means, against the radial artery 30 under the body surface or skin 12 of the subject. The control device 32 also functions as inflection-point determining means for determining a point of inflection, H, of a curve, $T_{DIA}$, representing a relationship between "provisional" diastolic blood pressure values $P_{DIA}$ measured by the pulse wave sensor 20 and chamber pressure values HDP measured by the air-pressure sensor 27 while the chamber pressure HDP is continuously changed by the control device 32 as the pressing-force determining means. The control device 32 also functions as correction-value determining means for determining a correction value, $K_S$, based on a provisional diastolic blood pressure value, $P_H$, of the determined point of inflection H. The control device 32 further functions as blood-pressure determining means for determining a "true" intra-arterial blood pressure value $P_{BP}$ of the artery 30 by subtracting the determined correction value $K_S$ from each provisional blood pressure value, Pa, measured by the pulse wave sensor, i.e. pressure sensor 20 pressed at the optimum chamber pressure $HDP_S$, i.e., optimum pressing force of the pressing device 10, 18, 24, 26.

Hereinafter, there will be described the blood pressure measuring operation of the present monitor system 8, by reference to the flow charts of FIGS. 3 and 4.

Upon application of electric power to the present monitor system 8, an initialization step (not shown) is carried out. Then, if a start/stop button (not shown) is operated, the CPU 34 of the control device 32 starts with Step S1 to judge whether a flag, F, is set at "1" i e F=1. That the flag F is set at F=1 means that the optimum chamber pressure $HDP_S$ and the optimum PS element 31a have been determined and selected.

Figure 5:
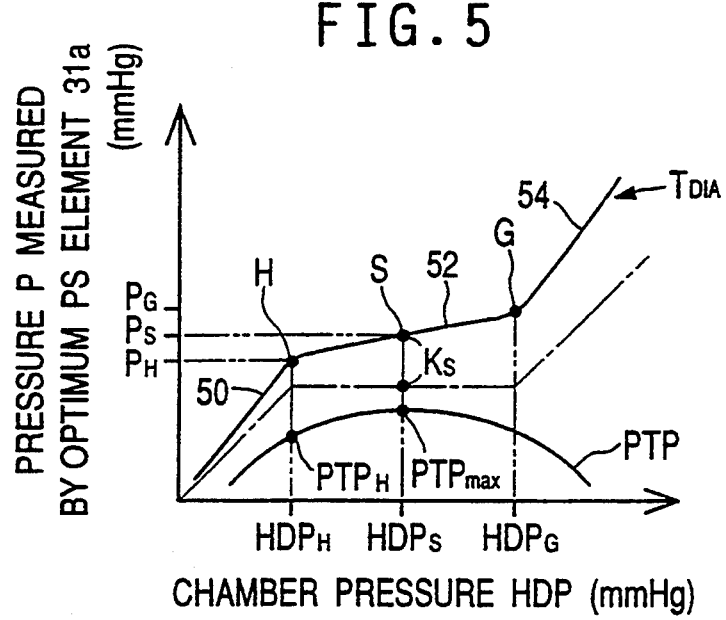
FIG. 5 is a graph showing a curve, $T_{DIA}$, representing a relationship between chamber pressure values, HDP, and provisional diastolic blood pressure values, $P_{DIA}$, which curve is obtained at Step S4-1 of FIG. 4.

Assuming that a negative judgment is made at Step S1, the control of the CPU 34 goes to Step S2 to determine the optimum chamber pressure $HDP_S$ and subsequently to Step S3 to select the optimum PS element 31a. For example, these operations are carried out in the following manner: After the chamber pressure HDP has been decreased down to a sufficiently low level by controlling the pressure regulator valve 26 and thereby discharging the air from the pressure chamber 22, the chamber pressure HDP is slowly increased up to a predetermined level at a suitable rate of change, so that the pulse wave sensor 20 is pressed with the increasing pressing forces against the radial artery 30 via the skin 12. During this pressing force increasing operation, the CPU 34 reads in the respective pulse wave signals SM supplied from the individual PS elements 31 of the pulse wave sensor 20, together with the pressure signal SP supplied from the air-pressure sensor 27. As described above, the pressure signal SP represents the slow and monotonous increasing of the chamber pressure HDP of the pressure chamber 22. The CPU 34 calculates, from each of the thus obtained pulse wave signals SM, the amplitude of each of successive pulses corresponding to heartbeats of the subject and selects, as the optimum PS element 31a, one of the thirty PS elements 30 which has detected a maximum pulse having the greatest amplitude of all the calculated amplitudes. The amplitude of each pulse is calculated by subtracting the magnitude of the lower peak of each pulse from the magnitude of the upper peak of the same pulse. The CPU 34 additionally determines, as the optimum chamber pressure $HDP_S$, a chamber pressure HDP at the time when the maximum pulse has been detected by the optimum PS element 31a. The thus determined optimum chamber pressure $HDP_S$ is stored in the RAM 38. In the graph of FIG. 5, the optimum chamber pressure $HDP_S$ corresponds to an upper peak, $PTP_{max}$, of a curve, PTP, representing the change of the respective amplitudes of the successive pulses of the pressure pulse wave represented by the pulse wave signal SM supplied from the optimum PS element 31a.

Figure 4:
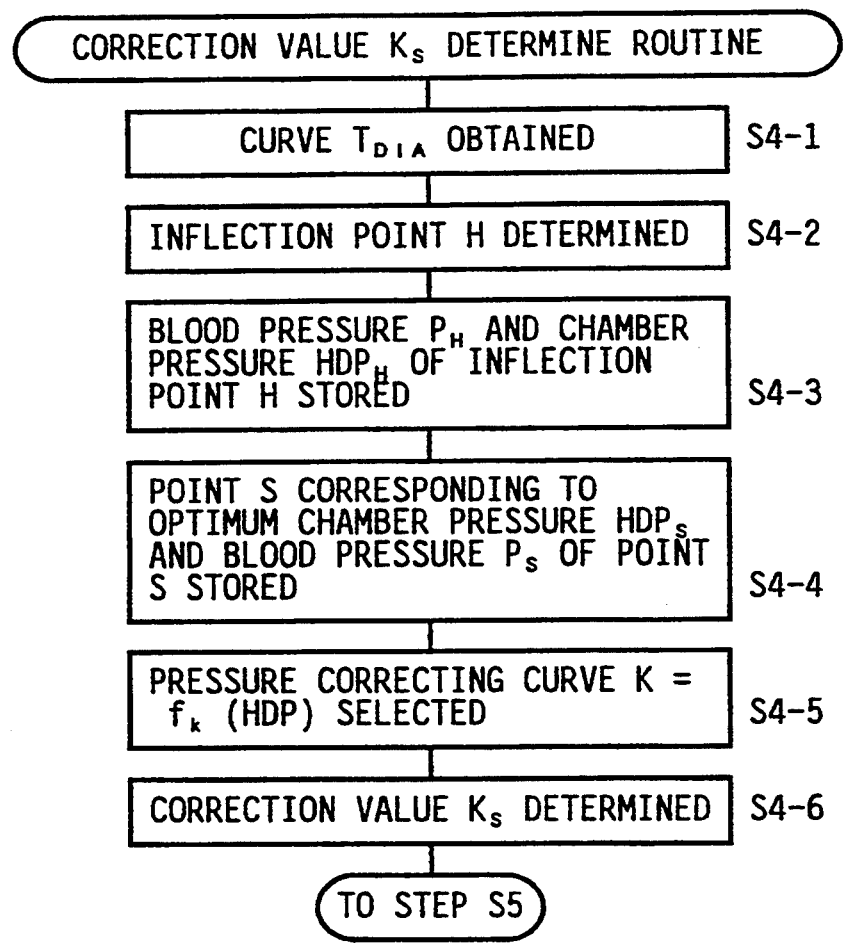
FIG. 4 is a flow chart representing the correction value determine routine carried out at Step S4 of FIG. 3.

Step S3 is followed by Step S4, i.e., correction value determine routine shown in FIG. 4. First, at Step S4-1 of the flow chart of FIG. 4, the CPU 34 determines a curve $T_{DIA}$, indicated at solid line in FIG. 5, which represents a relationship between the provisional diastolic blood pressure values $P_{DIA}$ measured by the pulse wave sensor 20 and the chamber pressure values HDP measured by the air-pressure sensor 27 while the chamber pressure HDP is continuously increased at Step S2 under the control of the CPU 34. The curve $T_{DIA}$ is obtained by smoothly connecting the respective lower-peak points of the successive pulses of the pressure pulse wave represented by the pulse wave signal SM supplied from the optimum PS element 31a.

The curve $T_{DIA}$ includes an increasing portion 50, and a level portion 52 called "plateau" which appears following the increasing portion 50 during the chamber pressure increasing operation carried out at Step S2. Subsequently, at Step S4-2, the CPU 34 determines an inflection point H connecting the increasing portion 50 and the level portion 52 of the curve $T_{DIA}$. For example, the inflection point H is determined by identifying a point where the slopes (i.e., differential values) of the curve $T_{DIA}$ significantly largely decreases, i.e., identifying an upper-peak point of a curve representing the change of slopes of the curve $T_{DIA}$, according to an algorithm prestored in the ROM 36. At the following Step S4-3, the CPU 34 stores, in the RAM 38, a provisional diastolic blood pressure value $P_H$ and a chamber pressure value $HDP_H$ of the thus determined inflection point H. Step S4-3 is followed by Step S4-4 to determine a point, S, of the curve $T_{DIA}$ corresponding to the stored optimum chamber pressure $HDP_S$ and store, in the RAM 38, a provisional blood pressure value $P_S$ corresponding to the thus determined point S.

Figure 6:
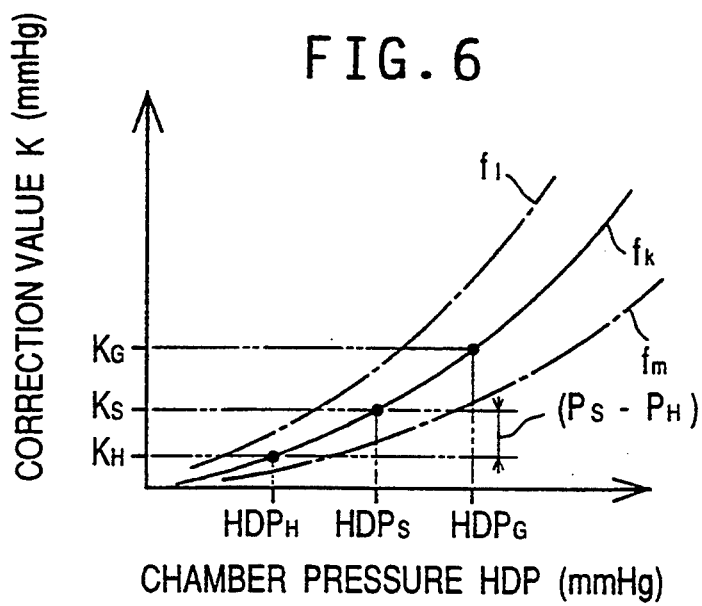
FIG. 6 is a graph showing a pressure correcting curve, $f_k$, selected at Step S4-5 of FIG. 4.

Subsequently, the control of the CPU 34 goes to Step S4-5 to select one of a plurality of relationships, $K=f_n(HDP)$ where $n=1, 2, 3, \ldots, m$), pre-stored in the ROM 36, in such a manner that the selected one relationship, $K=f_k(HDP)$, indicated at solid line in FIG. 6, provides the same difference, $K_S-K_H$, between a correction value, $K_S$, corresponding to the stored optimum chamber pressure value $HDP_S$ and a correction value, $K_H$, corresponding to the stored chamber pressure value $HDP_H$, as the difference, $P_S-P_H$, between the stored pressure values $P_S$, $P_H$ corresponding to the points S, H, respectively. Step S4-5 is followed by Step S4-6 to determine the correction value $K_S$ corresponding to the stored optimum chamber pressure value $HDP_S$, according to the thus selected relationship, i.e., pressure correcting curve $K=f_k(HDP)$. The thus determined correction value KS corresponds to the distance or difference between the point S and a one-dot chain line shown in the graph of FIG. 5. The one-dot chain line represents an ideal or theoretical curve $T_{DIA}$, which would be obtained by directly applying the pulse wave sensor 20 to the radial artery 30 with the skin tissue 12 being removed.

The pressure correcting curve $K=f_n(HDP)$ represents a relationship between chamber pressure values HDP, and "additional" pressure values added to "true" intra-arterial blood pressure values because of the elasticity of the subcutaneous tissue 12 located between the radial artery 12 and the pulse wave sensor 20 (i.e., each PS element 31). The additional pressure values increase as the chamber pressure values HDP increase, as shown in FIG. 6. This relationship $K=f_n(HDP)$ varies depending upon the elastic characteristic of the subcutaneous tissue of an individual living subject. The various relationships or curves $K=f_n(HDP)$ are obtained by experiments. Since the additional pressure values, i.e., correction values K are a non-linear function of the chamber pressure values HDP, each curve $K=f_n(HDP)$ may be approximated by, e.g., a quadratic function, $K=a\cdot(HDP)^2+b\cdot(HDP)+c$, where a, b, and c are constants. The curves $K=f_n(HDP)$ represented by the corresponding quadratic functions are indicated at one-dot chain line in FIG. 6.

Figure 3:
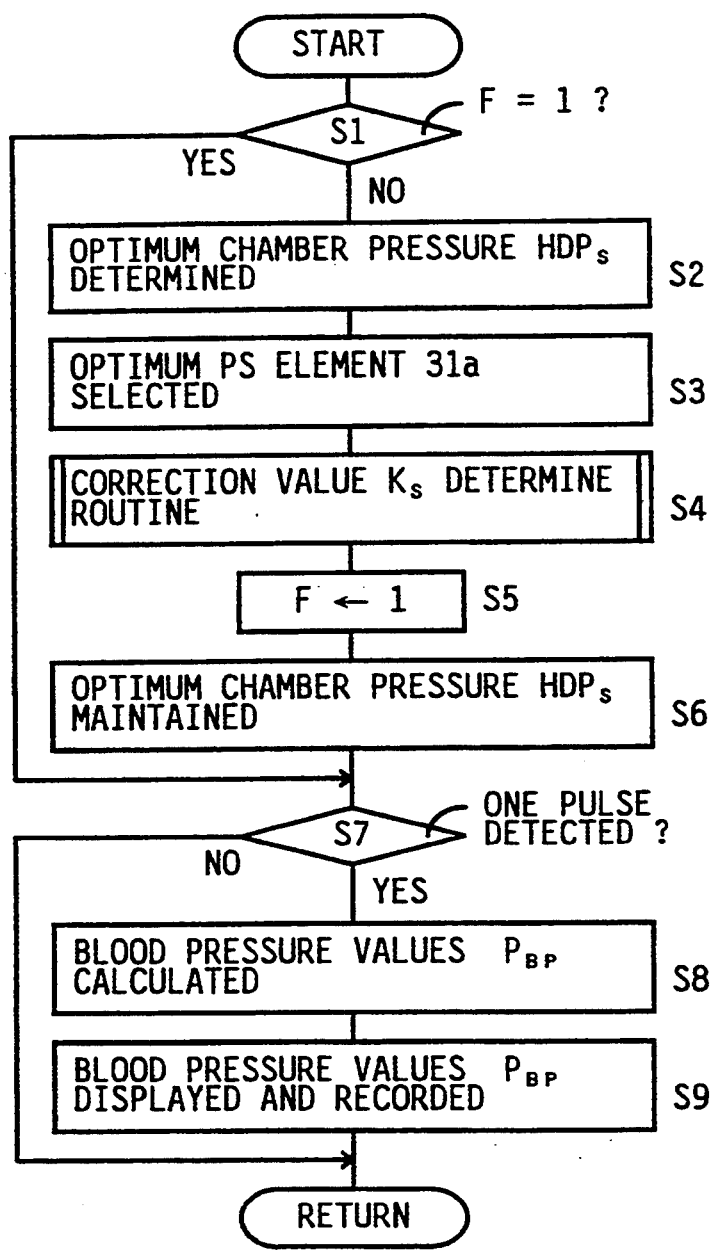
FIG. 3 is a flow chart representing a control program according to which a control device of the monitor system of FIG. 1 operates.

The pressure value determine routine of Step S4 is followed by Step S5 of FIG. 3. At this step, the CPU 34 sets the flag F to $F=1$. Subsequently, the control of the CPU 34 goes to Step S6 to control the pressure regulator valve 26 so as to press the pulse wave sensor 20 at the optimum chamber pressure $HDP_S$. Thus, the optimum chamber pressure $HDP_S$ is maintained at the optimum value $HDP_S$. Step S6 is followed by Step S7 to judge whether the CPU 34 receives, from the optimum PS element 31a, a length or amount of the pulse wave signal SM representing one pulse corresponding to one heartbeat of the subject. Steps S8 and S9 are not carried out so long as a negative judgment is made at Step S7. If a positive judgment is made at this step, the control of the CPU 34 goes to Step S8 to calculate a "true" blood pressure value $P_{BP}$ of the subject, according to the following, pressure correcting expression (1):

$$P_{BP}=P_a-K_S \qquad (1)$$

The CPU 34 determines the "true" or intra-arterial blood pressure value $P_{BP}$ of the artery 30 by subtracting the determined correction value $K_S(=f_k(HDP_S))$ from the provisional blood pressure value Pa measured by the pulse wave sensor 20 or optimum PS element 31a pressed at the optimum chamber pressure $HDP_S$. The thus determined blood pressure value $P_{BP}$ is stored in the RAM 38. The true blood pressure values $P_{BP}$ are continuously determined and stored in very short sampling cycles, so as to provide a corrected pulse wave which changes in synchronism with the heartbeats of the subject. The CPU 34 determines, as systolic and diastolic blood pressure values, $P_{SYS}$ and $P_{DIA}$, the respective blood pressure values of the upper and lower peaks of each of successive pulses of the corrected pulse wave, according to a well-known algorithm pre-stored in the ROM 36. The thus determined systolic and diastolic blood pressure values $P_{SYS}$ and $P_{DIA}$ are stored in the RAM 38.

Subsequently, the control of the CPU 34 goes to Step S9 to control the output device 40 to display the waveform of the corrected pulse wave, i.e., "true" blood pressure values $P_{BP}$ obtained at Step S8 of the current control cycle, following the waveform which had been obtained at Step S8 in the control cycles prior to the current control cycle. In addition, the output device 40 is operated to display, in digits, the systolic and diastolic blood pressure values $P_{SYS}$, $P_{DIA}$ determined at Step S8, and add a point (or symbol) representing each of the values $P_{SYS}$, $P_{DIA}$ to a corresponding one of respective time-wise changes of the points (or symbols) $P_{SYS}$, $P_{DIA}$.

It emerges from the foregoing description that, in the present embodiment, Step S4-2 and a portion of the control device 32 for carrying out Step S4-2 function as the inflection-point determining means for determining the inflection point H of the curve $T_{DIA}$ representing the relationship between the pressing forces HDP of the pressing device 10, 18, 24, 26 and the provisional blood pressure values Pa measured by the pulse wave sensor 20 as the pressure sensor while the pressing forces or chamber pressure values HDP are continuously changed, that Step S4-6 and a portion of the control device 32 for carrying out Step S4-6 function as the correction-value determining means for determining the correction value $K_S$ based on the provisional blood pressure value $P_H$ measured by the pulse wave sensor 20 and corresponding to the determined inflection point H, and that Step S8 and a portion of the control device 32 for carrying out Step S8 function as the blood-pressure determining means for operating the pressing device 10, 18, 24, 26 to maintain the optimum pressing force or chamber pressure $HDP_S$ and thereby press the pulse wave sensor 20 against the radial artery 30 and continuously determining the true intra-arterial blood pressure values $P_{BP}$ of the artery 30 by subtracting the correction value $K_S$ from the provisional blood pressure values $P_a$ measured by the pulse wave sensor 20 at the body surface or skin 12 of the subject.

Since the soft and elastic subcutaneous tissue 12 exists between the radial artery 30 and the pulse wave sensor 20, the provisional blood pressure value Pa measured by the optimum PS element 31a positioned directly above the artery 30 and pressed at the optimum pressing force $HDP_S$ contains both the true intra-arterial blood pressure value $P_{BP}$ of the artery 30 and the additional pressure value increased by the elastic force of the subcutaneous tissue 12. However, in the present blood pressure monitor system 8, the true intra-arterial blood pressure value $P_{BP}$ of the artery 30 is determined with high accuracy by subtracting, from the provisional blood pressure value $P_a$ measured by the pulse wave sensor 20, the correction value $K_S$ approximating the additional pressure resulting from the elastic force of the subcutaneous tissue 12.

While the present invention has been described in its preferred embodiment, the present invention may otherwise be embodied.

For example, although in the illustrated embodiment the inflection point H of the curve $T_{DIA}$ is determined at Step S4-2 and the correction value $K_S$ is determined based on the pressure value $P_H$ of the inflection point H at S4-6, it is possible to determine, as an inflection point of the curve $T_{DIA}$, a point, G, connecting the level portion 52 and a second increasing portion 54 at Step S4-2, and determine a correction value $K_S$ based on a pressure value, $P_G$, of the inflection point G at Step S4-6. In the latter case, at Step S4-5, the CPU 34 selects one of the pressure correcting curves $K=f_n(HDP)$ in such a manner that the selected one curve $K=f_k(HDP)$ provides the same difference, $K_G-K_S$, between a correction value, $K_G$, corresponding to the pressure value $P_G$ and the correction value $K_S$ corresponding to the optimum chamber pressure value $HDP_S$, as the difference, $P_G-P_S$, between the pressure values $P_G$, $P_S$ corresponding to the points G, S, respectively.

While both in the illustrated embodiment and the above-indicated modified embodiment the curve $T_{DIA}$ is obtained to determine the inflection point H or G at Step S4-1, it is possible to obtain, at Step S4-1, a curve $T_{SYS}$ by smoothly connecting the respective upper-peak points of successive pulses of the pressure pulse wave represented by the pulse wave signal SM supplied from the optimum PS element 31a. In the latter case, an inflection point corresponding to the point H or G is determined on the curve $T_{SYS}$ at Step S4-2, and a correction value $K_S$ is determined based on a provisional blood pressure value P of the determined inflection point.

In the illustrated embodiment, at Step S2, the optimum pressing force or chamber pressure $HDP_S$ is determined by identifying the pressing force or chamber pressure HDP at the time of detection of the maximum pulse by the optimum PS element 31a of the pulse wave sensor 20. It is known that the pressing force HDP at the time of detection of the maximum pulse well corresponds to the middle point of the level portion 52 of the curve $T_{DIA}$. Therefore, at Step S2, it is possible to identify the middle point of the level portion 52 of the curve $T_{DIA}$ and determine a pressing force or chamber pressure HDP of the identified middle point, as the optimum pressing force or chamber pressure $HDP_S$.

In the illustrated embodiment, at Step S4-2, the inflection point H of the curve $T_{DIA}$ is determined by identifying a point where the slopes of the curve $T_{DIA}$ significantly largely changes. However, it is possible to determine the inflection point H of the curve $T_{DIA}$ by identifying a point, $PTP_H$, of the pulse-amplitude curve PTP, as shown in FIG. 5. The point $PTP_H$ has an amplitude smaller by a predetermined proportion (e.g., about 10%) than the maximum amplitude $PTP_{max}$ of the curve PTP, and corresponds to a pressing force HDP smaller than the optimum pressing force $HDP_S$. In this case, the inflection point H of the curve $T_{DIA}$ corresponds to the pressing force HDP of the point $PTP_H$.

In the illustrated embodiment, at Step S4, the pressure correcting curves $K=f_n(HDP)$ represented by the quadratic functions are used. However, in place of the quadratic functions, logarithmic or exponential functions may be used to represent the curves $K=f_n(HDP)$. Since, actually, only particular portions of the curves $K=f_n(HDP)$ corresponding to low chamber pressure values HDP in the graph of FIG. 6 are used, the curves $K=f_n(HDP)$ may be approximated by linear functions.

While in the illustrated embodiment Step S7 is provided, before Steps S8 and S9, to wait for supplying of each one pulse of the pulse wave signal SM, i.e., pressure pulse wave, Step S7 may be omitted.

It is to be understood that the present invention may be embodied with other changes, improvements, and modifications that may occur to those skilled in the art without departing from the spirit and scope of the present invention defined in the appended claims.

What is claimed is:

1. A blood pressure monitor system comprising:
a pressure sensor having a press surface and including at least one pressure sensing element provided in said press surface;
a pressing device which presses said pressure sensor against an arterial vessel of a living subject via a body surface of the subject so that said pressure sensing element of the pressure sensor measures a pressure value at said body surface of the subject;
pressing-force determining means for determining an optimum pressing force of said pressing device at which a portion of a wall of said arterial vessel of the subject is flattened under said pressure sensor pressed by the pressing device;
inflection-point determining means for changing pressing forces of said pressing device applied to said pressure sensor, and determining a point of inflection of a curve representing a relationship between the changed pressing forces of the pressing device and pressure values measured by the pressure sensor at said body surface of the subject;
correction-value determining means for determining a correction value based on the pressure value of the determined point of inflection; and
blood-pressure determining means for operating said pressing device to maintain the determined optimum pressing force and press said pressure sensor against said arterial vessel of the subject via said body surface of the subject, and continuously determining intra-arterial blood pressure values of the arterial vessel of the subject by subtracting said correction value from the pressure values measured by the pressure sensor at the body surface of the subject.

2. A monitor system according to claim 1, wherein said correction-value determining means comprises:
a memory which stores a plurality of pressure correcting curves each of which represents a relationship between correction values and pressing forces of said pressing device;
selecting means for selecting one of said pressure correcting curves which provides a same difference between a first correction value corresponding to the pressing force of said determined point of inflection and a second correction value corresponding to said determined optimum pressing force of said pressing device, as an actual difference between the pressure value of said point of inflection and the pressure value corresponding to said optimum pressing force of the pressing device; and determining means for determining, as said correction value, said second correction value corresponding to said optimum pressing force of the pressing device, according to the selected one pressure correcting curve.

3. A monitor system according to claim 2, wherein said memory of said correction-value determining means stores said pressure correcting curves each of which is defined by a quadratic function.

4. A monitor system according to claim 2, wherein said memory of said correction-value determining means stores said pressure correcting curves each of which is defined by a linear function.

5. A monitor system according to claim 1, wherein said pressure sensor comprises a pulse wave sensor which has said press surface and which detects a pressure pulse wave including a plurality of successive pulses produced from said arterial vessel of said subject in synchronism with heartbeats of the subject and transmitted to said press surface of said pulse wave sensor via said body surface of the subject.

6. A monitor system according to claim 5, wherein said pulse wave sensor comprises a semiconductor chip having said press surface, and a plurality of pressure sensing elements as said at least one pressure sensing element, said pressure sensing elements being provided in an array in said press surface of said semiconductor chip, said array of pressure sensing elements being adapted to intersect said arterial vessel of the subject with said pulse wave sensor being pressed against the arterial vessel of the subject via said body surface of the subject.

7. A monitor system according to claim 5, wherein said pressing device comprises:
a housing having an open end;
a flexible diaphragm closing said open end of said housing and thereby defining a fluid-tight chamber in the housing, said pressure sensor being secured to an outer surface of said diaphragm;
a fluid supply which supplies a pressurized fluid to said fluid-tight chamber of said housing to press said pulse wave sensor against said arterial vessel of said subject via said body surface of the subject; and
a pressure regulator which regulates a fluid pressure in said fluid-tight chamber of said housing.

8. A monitor system according to claim 7, wherein said pressing-force determining means comprises:
a fluid-pressure sensor which measures said fluid pressure in said fluid-tight chamber of said housing; and
means for determining, as said optimum pressing force of said pressing device, the fluid pressure measured by said fluid-pressure sensor at a time when said pulse wave sensor has detected a maximum pulse having a greatest amplitude of the successive pulses of said pressure pulse wave detected by the pulse wave sensor while said fluid pressure of said fluid-tight chamber is continuously changed.

9. A monitor system according to claim 5, wherein said inflection-point determining means comprises means for determining, as said curve, a curve representing a relationship between said changed pressing forces of said pressing device and provisional diastolic blood pressure values measured by said pulse wave sensor at said body surface of said subject, said provisional diastolic blood pressure values corresponding to respective lower peaks of the successive pulses of said pressure pulse wave detected by the pulse wave sensor while the pressing force of the pressing device is continuously changed.

10. A monitor system according to claim 5, wherein said inflection-point determining means comprises means for determining, as said curve, a curve representing a relationship between said changed pressing forces of said pressing device and provisional systolic blood pressure values measured by said pulse wave sensor at said body surface of said subject, said provisional systolic blood pressure values corresponding to respective upper peaks of the successive pulses of said pressure pulse wave detected by the pulse wave sensor while the pressing force of the pressing device is continuously changed.

11. A monitor system according to claim 5, wherein said blood-pressure determining means comprises means for successively determining, as said intra-arterial blood pressure values of said arterial vessel of said subject, at least one of a systolic and a diastolic blood pressure value by subtracting said correction value from at least one of provisional systolic and diastolic blood pressure values corresponding to the upper and lower peaks of each of the successive pulses of said pressure pulse wave detected by the pulse wave sensor.

12. A monitor system according to claim 11, further comprising an output device including at least one of (a) a display which displays at least one of (i) digits representing each of the successively determined values of said at least one of said systolic and diastolic blood pressure, (ii) symbols representing a time-wise change of said successively determined values of said at least one of said systolic and diastolic blood pressure, (iii) a waveform of the continuously determined intra-arterial blood pressure, and (b) a recorder which records, on a recording medium, at least one of (i) digits representing each of the successively determined values of said at least one of said systolic and diastolic blood pressure, (ii) symbols representing a time-wise change of said successively determined values of said at least one of said systolic and diastolic blood pressure, (iii) a waveform of the continuously determined intra-arterial blood pressure.

13. A monitor system according to claim 1, wherein said inflection-point determining means comprises means for determining, as said point of inflection, a point of said curve between a plateau region of said curve and an increasing portion of said curve, where the slopes of the plateau region and the increasing portion significantly differ.

* * * * *